United States Patent [19]

Saunders

[11] Patent Number: 4,755,267
[45] Date of Patent: Jul. 5, 1988

[54] METHODS AND APPARATUS FOR PROTECTING METAL STRUCTURES

[75] Inventor: David N. Saunders, North Berwick, Me.

[73] Assignee: Pennwalt Corporation, Philadelphia, Pa.

[21] Appl. No.: 870,253

[22] Filed: Jun. 3, 1986

[51] Int. Cl.$^4$ .............................................. C23F 13/00
[52] U.S. Cl. ...................................... 204/147; 204/196
[58] Field of Search ................................ 204/196, 147

[56] References Cited

U.S. PATENT DOCUMENTS

| | | | |
|---|---|---|---|
| 2,982,714 | 5/1961 | Sabins | 204/196 |
| 3,197,755 | 7/1965 | Conger | 204/196 |
| 3,425,921 | 2/1969 | Sudrabin | 204/147 |
| 3,461,051 | 8/1969 | Vrable | 204/196 |
| 3,634,222 | 1/1972 | Stephens | 204/196 |
| 4,080,565 | 3/1978 | Polak et al. | 324/71 R |
| 4,160,171 | 7/1979 | Merrick | 307/95 |
| 4,255,242 | 3/1981 | Freeman | 204/147 |
| 4,383,900 | 5/1983 | Garrett | 204/147 |
| 4,391,841 | 7/1983 | Zeblisky | 204/196 |
| 4,409,080 | 10/1983 | Slough | 204/196 |
| 4,437,957 | 3/1984 | Freeman | 204/147 |
| 4,457,821 | 7/1984 | Sudrabin et al. | 204/196 |
| 4,481,474 | 11/1984 | Gerrit | 204/196 |
| 4,489,277 | 12/1984 | Goolsby | 204/196 |

Primary Examiner—John F. Niebling
Assistant Examiner—Steven P. Marquis
Attorney, Agent, or Firm—Panitch Schwarze Jacobs and Nadel

[57] ABSTRACT

Corrosion prevention methods and apparatus are disclosed for protecting a metal structure immersed in a corroding electrolyte wherein a continuously applied filtered direct current is passed therethrough. A reference electrode or cell, preferably one, is immersed with the electrolyte between anode means and the structure wall but spaced a considerable distance from the wall. The metal structure potential is sensed and measured against the reference electrode, free of IR drop effect of the protective current and electrolyte resistivity variations, by automatic and periodic modulation of the protective current. Calculations are suitably made by a microprocessor-based controller which also regulates the protective current for maintaining a selected structural potential.

30 Claims, 2 Drawing Sheets

METHODS AND APPARATUS FOR PROTECTING METAL STRUCTURES

STATEMENT OF THE INVENTION

This invention relates to cathodic and anodic protection systems, and more particularly to methods for deducing the polarization potential at the interior surface of a metal structure to be protected which immerses a corroding electrolyte. Deductions or measurements are made from separate voltage measurements provided preferably by a single reference electrode placed within the electrolyte and distant from the structure surface to be protected.

BACKGROUND OF THE INVENTION

Corrosion of a metal structure immersed in an electrolyte results from flow of local current through the electrolyte between localized anodic and cathodic portions of the structure surface, the corrosion occurring at the anodic surface portions. A familiar example is the corrosion of iron or iron alloy structures immersed in water. Prevention of such corrosion by cathodic protection involves passing direct current (applied by a suitable current source) through the electrolyte from one or more anodes immersed therein to the metal structure to be protected, which is connected to the negative terminal of the current source to constitute the cathode of the system. The purpose of providing this applied current is to establish and maintain at the structure surface, including the localized anodic portions thereof, a negative polarization potential effective to prevent the corrosion-producing local current flow.

Since the effectiveness of a cathodic protection system is dependent on maintenance of a sufficient electronegative polarization potential at the structure to be protected, it is desirable to control the operation of the cathodic protection system, as by adjustment of the applied current flow, in response to changes in the structure potential. Such control may be accomplished by measuring the structure potential and actuating appropriate control means in accordance with the potential measurement to vary the current supply from the direct current source so as to maintain the polarization potential at a desired value.

If the electrolyte in which the protected structure is immersed has a sufficiently low resistivity, the polarization potential of the structure may conveniently be determined by immersing in the electrolyte a suitable non-polarized reference electrode of fixed potential and directly measuring the difference of potential between this reference electrode and the structure. In such circumstance, the potential drop through the electrolyte between the reference electrode and the structure is so small as to be negligible in its effect on control of the system, i.e., variations in the potential difference between the electrode and structure are due substantially only to variations in structure polarization potential and hence provide effective system control.

However, when the resistivity of the electrolyte is high (e.g., greater than about 1,000 ohm-centimeters, as in the case of electrolytes such as potable waters) the potential difference measured between the reference electrode and the structure includes a significant potential drop resulting from the flow of cathodic protection current through the resistive electrolyte between the electrode and structure. This potential drop varies with changes in the applied current and/or in the resistivity of the electrolyte. As a result, in operation in a high-resistivity electrolyte, utilizing measurement of potential difference between a reference electrode and the protected structure to control the operation of a cathodic protection system as heretofore known, the system responds to variations in electrolyte resistivity or applied current density as well as to variations in the polarization potential of the protected structure. This is undesirable, since the potential drop resulting from applied current flow through the electrolyte has little or no relation to the effectiveness of control of local current flow at the metal surface to be protected; accordingly, for proper regulation of a cathodic protection system to maintain a desired polarization potential at the structure surface, the determination or sensing of the polarization potential should be accomplished in a manner that is independent of the latter potential drop, i.e., which effectively eliminates variations in such potential drop as a control factor in the system.

While the undesired potential drop component of the polarization potential measurement can be very substantially reduced by placing the reference electrode on the protected surface, such arrangement presents difficulties in that the reference electrode then senses the potential of only a very limited area of the structure surface, and in addition the electrode may partially shield the surface from the applied protective current.

Difficulties similar to those described above are encountered in controlling anodic protection systems operating for passivation of metal surfaces (e.g., such as stainless steel surfaces) immersed in highly resistive electrolytes. In an anodic passivation system, the structure to be protected is connected to the positive terminal of a direct current source, the negative terminal of which is connected to auxiliary electrode means immersed in the electrolyte. To effect and maintain passivation of the structure surface, it is necessary that the structure potential (determined by comparison with standard reference electrode means) be controlled within a limited range of values, by regulation of the current source; if the structure potential departs from this range, the anodic protection operation may actually enhance the rate of structure corrosion. As in the case of cathodic protection, it is desirable to eliminate, from the measurement of structure potential used for system control, variables due to electrolyte resistivity and current density, which may be introduced in the measurement if the electrolyte resistivity is sufficiently high to provide an appreciable potential drop between the measuring reference electrode means and the structure through the electrolyte.

THE PRESENT INVENTION

The present invention is an improvement upon the invention disclosed in U.S. Pat. No. 3,425,921, for "Methods and Systems for Protecting Metal Structures", issued to Leon P. Sudrabin, and assigned to Pennwalt Corporation, the assignee of the present invention, through mesne assignments.

THE SUDRABIN INVENTION

In the patent to Sudrabin, U.S. Pat. No. 3,425,921, incorporated herein by reference, two reference electrodes are immersed in the electrolyte in spaced relation to each other and to the tank and anodes. The reference electrodes are so positioned that the potential drop resulting from passage of current between the reference electrode disposed farther from the tank wall and the tank through the electrolyte is greater than the potential drop resulting from passage of current between the reference electrode positioned closer to the tank wall and the tank through the electrolyte.

The polarization potential $V_p$ is obtained by means of a Wheatstone bridge and null meter/meter relay according to the following equation where cell 3 and cell 2 indicate the reference electrodes disposed closer from, and farther to, the tank wall respectively:

$$V_p = V_{2a} - I_a k_1 k_2$$

where $V_p$ = polarization potential,
$V_{2a}$ = cell 2 voltage
with anode current $I_a$ applied, $k_1$ represents a constant introduced by the setting on the front panel of potentiometer 25, i.e., when tap 29 is set such that no deflection of galvanometer 40 results when switch 53 is successively opened and closed, or, when the Wheatstone bridge is balanced, and $k_2$ presents the cell 3 IR drop/cell 2 IR drop.

Since the IR drop at any point within the protected structure is a linear function of applied anode current, the cell 3 IR drop may be regarded as a fixed constant times the cell 2 IR drop.

Thus, at unit setup, the operator proceeds to "balance the Wheatstone bridge" comprising making adjustments to the balance control potentionmeter and by forced step changes in the anode current via the modulation control described. The balance condition may thus be expressed by the equation:

$$k_1 k_2 = \frac{V_{2b} - V_{2a}}{I_b - I_a}$$

where $V_{2a}$ is cell 2 voltage with anode current $I_a$ applied,
$V_{2b}$ is cell 2 voltage with anode current $I_b$ applied,
and where current level $I_a$ is distinct from current level $I_b$, and where current level $I_a$ is equal to the normal operating current, namely current level $I_A$.

When constant $k_1$ is adjusted so that the balance condition just referred to is satisfied, changes in anode current cause no change in calculated polarization potential. Once constant $k_1$ is set, it is retained mechanically as the set position of the balance control potentiometer. A null voltmeter is used to indicate very slight changes in calculated polarization potential with changes in anode current.

The factor $k_2$, i.e., the ratio of cell 3 IR drop to cell 2 IR drop, can change slowly with the passage of time just as the condition of the protected structure changes with the passage of time. A change in the ratio however alters the bridge balance causing an error to be introduced into the calculation of the polarization potential. The error is corrected periodically by repeating the bridge-balancing procedure to thereby maintain as IR-drop-free measurement of the polarization potential.

ADVANTAGES AND SUMMARY OF THE PRESENT INVENTION

A measurement cell placed at the surface of the structure to be protected, as discussed and described in the aforediscussed Sudrabin patent, may alter the protective potential field in the vicinity of the cell leaving a small area of the surface underprotected or completely unprotected against corrosion. Additionally, a measurement cell placed at the surface of the structure will provide a very localized measurement of potential. Thus, if the surface coating on the structure is of variable quality, this measured potential may or may not accurately reflect the polarization at other points along the surface. Further, a measurement cell placed at the surface of the structure will measure some voltage drop due to the layer of fluid between the cell and the surface; this voltage drop is proportional to the distance from the cell to the surface, the applied protective current, and the resistivity of the fluid.

In the present invention, voltage measurements are taken at a distance from the surface and are therefore less affected by localized surface conditions. The polarization potential thus measured reflects the average potential over a larger area of the surface.

Briefly, in the present invention, a measurement cell or reference electrode, preferably one, is positioned within the electrolyte at a distance from the structure wall. The polarization potential at the structure wall is then deduced from voltage measurements taken from the cell. Since the cell is positioned away from the structure wall, the aforementioned disadvantages resulting from measurements taken from a surface positioned electrode or cell are avoided.

Further, the present invention performs through microprocessor-based controller calculations what the Sudrabin system and device performed by means of a Wheatstone bridge. Additionally, the present invention employs measurement techniques which provide for "rebalancing" on an automatic and periodic basis for maintaining an IR-drop-free environment and yet requires but a single reference electrode, although more than one may be employed, as compared to the matched pair required by Sudrabin.

DETAILED DESCRIPTION OF THE INVENTION

Particular reference to cathodic protection of metal structures is made herein rather than to protection thereof by anodic passivation.

Figure 2:
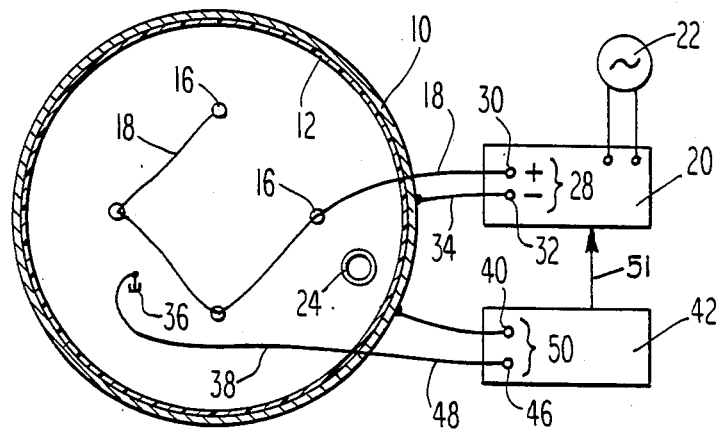
FIG. 2 is a sectional view of FIG. 1 taken along line 2—2 thereof.
Figure 1:
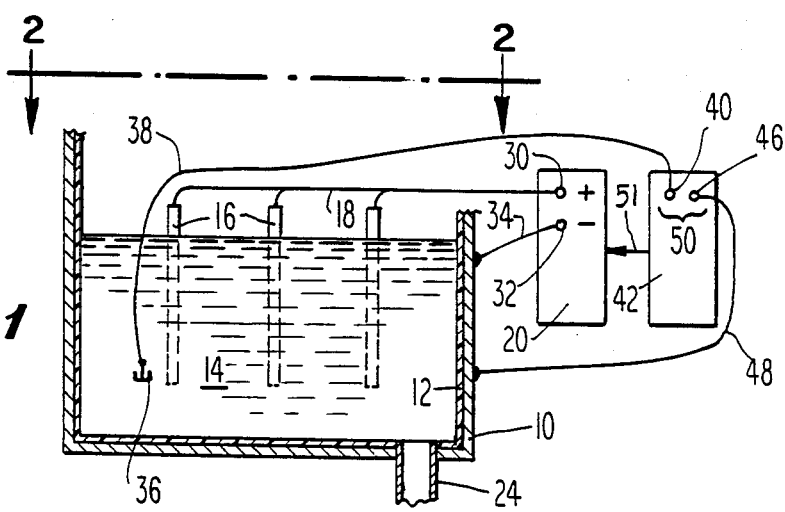
FIG. 1 is a sectional view of a metal structure to be protected, typically a water storage tank, roof omitted for purposes of clarity, schematically illustrating cathodic protection apparatus of the present invention employed with the tank.

In FIGS. 1 and 2, storage tank 10, typically steel, is optionally coated on its interior surface with an electrically resistant material 12. Tank 10 stores a corroding electrolyte 14, typically water. A plurality of anodes 16 is suspended vertically from a tank roof (not shown) and are shown connected serially by insulated wires 18 to the positive direct current terminal of an adjustable rectifier 20 which converts alternating current from alternating current source 22 to direct current. Adjustable rectifier 20 is suitably a potential control rectifier. It is appreciated that anodes 16 may be connected in parallel, and a greater or lesser number than the four anodes shown may be employed. It is further appreciated that more than one adjustable rectifier and more than one electrode circuit may be employed to produce total electrode current.

An inlet-outlet pipe 24 is provided at the bottom of tank 10.

The electrode current circuit 28 of rectifier 20 includes the positive direct current terminal 30 and the negative direct current terminal 32, the latter being connected to the tank 10, or vessel structure, through wire 34.

A saturated copper-copper sulfate reference electrode 36, for example, is suitably positioned within electrolyte 14 a considerable distance from the tank wall, and is connected by insulated wire 38 to terminal 40 of a microprocessor-based controller 42. The structure terminal 46 of controller 42 is connected to tank 10 through wire 48. The circuit through terminals 40 and 46 comprises control circuit 50. As is well known, direct current is passed through the electrolyte 14 from anodes 16 immersed therein to the metal structure to be protected which is connected to the negative terminal of the protective current circuit 28 to thereby maintain the necessary negative polarization potential at the structure surface to prevent or retard corrosion thereat. Control circuit 50 of microprocessor-based controller 42 modulates the current applied to the electrode current circuit through adjustable rectifier 20 indicated by arrow 51.

Figure 3:
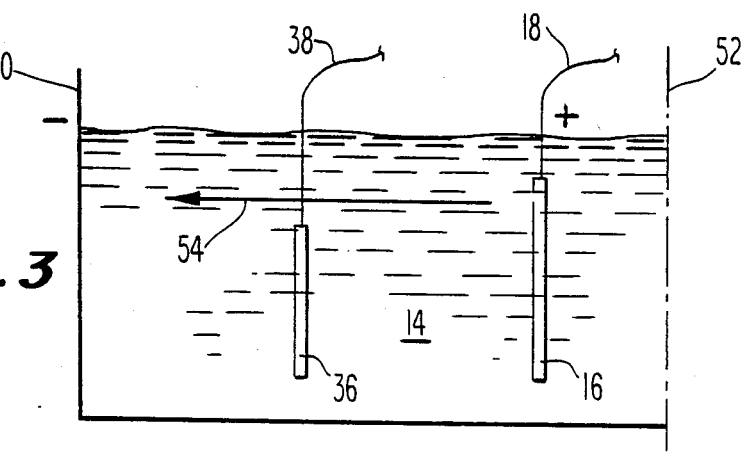
FIG. 3 is a diagrammatic representation of a portion of the drawing of FIG. 1.

In FIG. 3, cylindrical tank 10 is shown containing electrolyte 14 which immerses anode 16 and cell 36. Numeral 52 defines an approximate center line of the cylindrical tank and arrow 54 indicates the direction of flow of the protective current.

Figure 4:
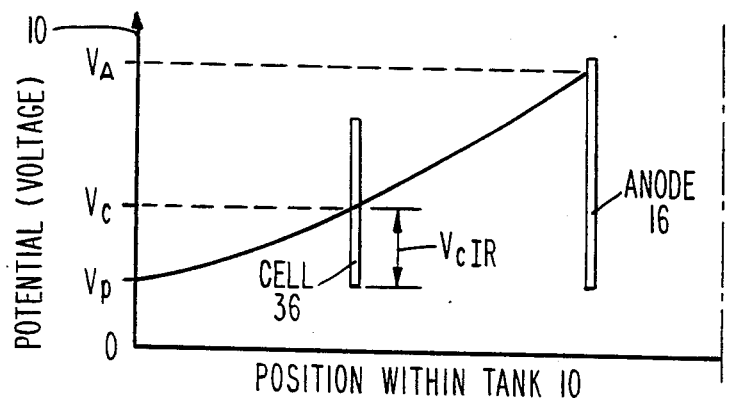
FIGS. 4 and 5 are graphical representations of potential versus the position of the anode and reference cell (within the tank) at various levels of applied anode current.

In FIG. 4, $V_A$ represents the anode 16 voltage; $V_p$, the potential at the interior surface of tank 10; and $V_c$, the voltage at the reference cell 36. The voltage at the cell consists of two components, namely, $V_p$ and $V_{cIR}$, the latter representing the IR voltage drop at the cell 36 position, i.e., the voltage drop between cell 36 and the tank wall. The tank or polarization potential, $V_p$, may now be calculated from measurements of $V_c$ and the level of electrode current, later described.

Since tank 10 is cylindrical, the potential at the interior surface of the tank versus cell 36 position is not linear. (It is appreciated that the present invention is equally applicable for tanks or structures other than cylindrical). For the cylindrical tank shown, tank 10 thus has a larger conductive area as the structure wall is approached. This larger conductive area, notwithstanding the presence of electrically resistant material 12 thereover, results in a smaller change in potential for a given difference in radial position of cell 36. The slope of potential $V_p$ at any point in FIG. 4 may be determined if the resistivity of the electrolyte is known, as well as the effective conductive area as determined by the configuration of the structure and the current which flows from anode 16 to the cathode, or tank 10.

Figure 5:
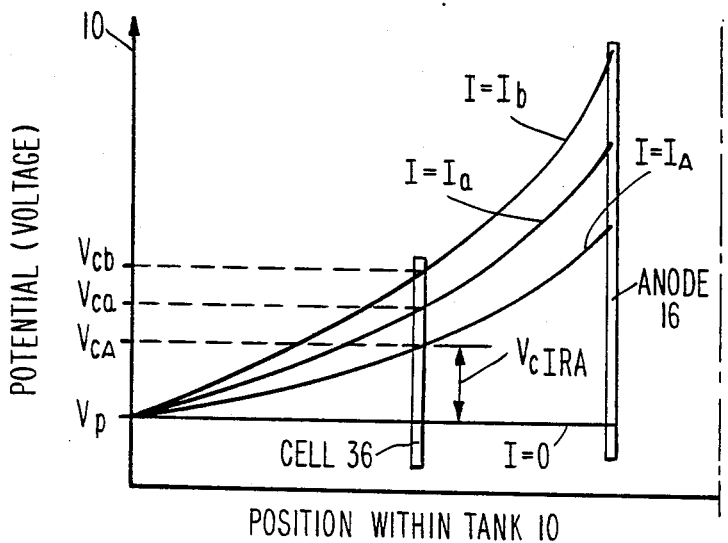

Thus, consider the potential function within the tank at two different levels of anode current (FIG. 5). Potential is plotted for electrode current levers "a" and "b". Voltages at cell 36 are designated $V_{ca}$ and $V_{cb}$ respectively. The potential function within the tank with no applied electrode current is a constant, $V = V_p$.

Polarization potential is a function of the protective electrode current level. Polarization potential, $V_p$, changes with a time constant on the order of ones of seconds, depending upon the specific combination of tank condition, current level, and fluid resistivity. Since $V_p$ is insensitive to rapid changes in current, i.e., changes made on the order of hundreds of milliseconds, or less, $V_p$ can be considered constant if the current level is abruptly changed from a steady state level "A" to a level "a" to a level "b". The present measurement technique requires that current levels "a" and "b" are distinct (not equal), and nonzero. However, either current level "a" or current lebel "b" may be equal to the steady state current level $I_A$, and further, current level "a" can be greater than current level "b", or current level "b" can be greater than current level "a". FIG. 5 thus depicts the measurement of $V_c$ under steady state conditions (with anode current $I_A$ applied, an abrupt change in current level to current level "a", a measurement of $V_c$ at current level "a", and an abrupt change in current level to current level "b", and a measurement of $V_c$ at current level "b"). While FIG. 5 shows (for graphical clarity) current levels "A", "a", and "b" as three distinct levels with current level "b" being greater than current level "a", and current level "a" being greater than current level "A", it is understood that no such limitation is imposed. It is further understood that current levels "a" and "b" may consist of any combination of protective current and measurement current. Here, protective current is defined as that current, produced from a set of at least one electrode, which has the principal function of protecting the structure from corrosion. Measurement current is defined as that current, produced from a set of at least one electrode, which has the principal function of modulating the electrode current for the purpose of measuring the change in cell voltage with change in electrode current. The protective current and measurement current may be produced by the same set of electrodes, or by separate sets of electrodes. Also, one set of electrodes may at different times produce varying combinations of protective and measurement current, and a distinct set of electrodes may produce another combination of protective and measurement current, such that the total electrode current is maintained constant, but the distribution of current within the electrolyte is altered, producing the modulated current levels $I_a$ and $I_b$ at the cell location. Further, the values for $V_{cA}$, $V_{ca}$, and $V_{cb}$ may be composite values from a set of at least one cells positioned within the electrolyte, said composite values being derived from the individual cell voltages by arithemetic summation or by averaging, for example.

It is appreciated that the present technique works well when current levels $I_a$ and $I_b$ are small deviations from $I_A$ (within 10% of $I_A$) so that continuous protection of the structure is maintained even during current modulation. Further, because the change in electrode current may be small, the resultant change in cell voltage may be correspondingly small, minimizing the transient effects on measurement of the cell voltage.

Figure 6:
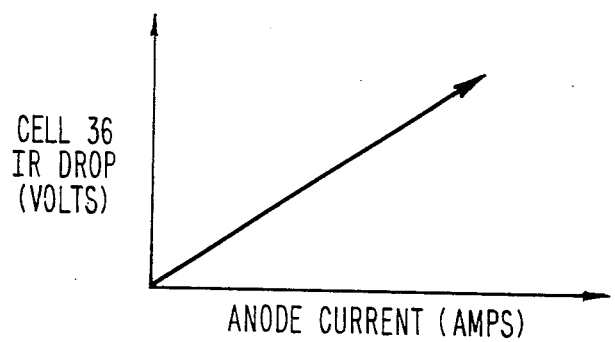
FIG. 6 graphically illustrates the linear relationship between reference cell IR drop and anode current.

While the polarization potential function is not considered to be linear with respect to the position of the components, the IR voltage drop however is a linear function of applied anode current. More specifically, the IR voltage drop component of the cell 36 voltage is linearly related to the anode current. Thus, if the anode current is doubled, the IR voltage drop component of the cell 36 voltage is similarly doubled. This relationship is illustrated in FIG. 6.

DETAILS OF THE MEASUREMENT TECHNIQUE OF THE PRESENT INVENTION

Let us consider making measurements on reference cell 36 at current levels $I_A$ (the steady state current level), $I_a$, and $I_b$, with the current level changing abruptly from current level "A" to current level "a" and again to current level "b" (but where either current level "a" or current level "b" may in fact be equal to the steady state current level "A"). Measurements are made of the values for $V_{ca}$, $V_{cb}$, $I_a$ and $I_b$. The graph of FIG. 5 is based on these measurements.

Polarization potential, Vp, may be defined by the equation:

$$V_p = V_{cA} - V_{cIRA} \quad (1)$$

where
$V_{cA}$ is the cell 36 voltage at current level $I_A$, and
$V_{cIRA}$ is the cell 36 IR drop at current level $I_A$.

Due to the linear relationship between the cell 36 IR drop with respect to the anode current, we have by a simple ratio:

$$\frac{V_{cIRA}}{I_A} = \frac{V_{cb} - V_{ca}}{I_b - I_a} \quad (2)$$

or $$V_{cIRA} = I_A \frac{V_{cb} - V_{ca}}{I_b - I_a} \quad (3)$$

where
$V_{cIRA}$ is the cell 36 IR drop at current $I_A$,
$V_{ca}$ is the cell 36 voltage at current $I_a$, and
$V_{cb}$ is the cell 36 voltage at current $I_b$.

Thus, the cell IR drop is calculable when given both of the cell voltages and the anode currents.

Substituting the value of $V_{cIRA}$ of Eq. 3 into Eq. 1 yields $$V_p = V_{cA} - I_A \frac{V_{cb} - V_{ca}}{I_b - I_a} \quad (4)$$

It is noted that the second term in Eq. 4, i.e., the value of $V_{cIRA}$, is the IR drop component of the cell voltage which can be deduced by modulating the current between the levels "a" and "b", and measuring the change in cell voltage as well as the change in anode current. The current may be modulated above the normal operating current, below the normal operating current, or both above or both below the normal operating current. Also, the modulation may be done more than one time, with measurements from the multiplicity of modulation cycles combined to produce values for $V_{ca}$, $V_{cb}$, $I_a$, and $I_b$ to be used in the above equations. The combination of the multiple measurements may be made by arithmetic summations, or by averaging, for example.

In cathodic protection apparatus having an electrically filtered output (to reduce electrical interference with other equipment), the current output does not respond immediately, but rather slowly, to commanded changes in current input. The current output is nevertheless measurable at all times enabling the value of $V_p$ to be determined by measurements of cell 36 voltage and levels of currents $I_a$ and $I_b$.

It is noted that a well coated surface of a tank immersing water therein having minute flaws in the surfaces may be protected against corrosion when a negative tank-to-water potential between 0.85 and 1.10 volts as measured between the well coated tank and a saturated copper-copper sulfate reference cell placed in the water adjacent the coated tank surface was maintained, as shown and described in U.S. Pat. No. 4,457,821, issued to Sudrabin et al., and incorporated herein by reference.

The present invention works equally well with poorly coated or uncoated tanks.

It is well known in control system theory that a measured potential as abovedescribed may be used as the feedback means in an automatic and continuous polarization potential controlling system by comparing said measured potential to a predetermined set point and adjusting the electrode current accordingly.

I claim:

1. A method for determining the polarization potential of a metal structure in contact with a corroding electrolyte, comprising
   continuously passing a flow of undirectional current to said structure through said electrolyte from electrode means positioned therein,
   establishing a measuring circuit comprising a voltage measuring means, current measuring means, a single reference cell, and said metal structure, said cell positioned in said electrolyte between said electrode means and a wall of said structure at a substantial distance therefrom,
   measuring said electrode current at a first level "a" and measuring voltage at said reference cell at said first level "a" of electrode current,
   varying said electrode current by modulation which abruptly changes said electrode current from said first level "a" to a second level "b",
   measuring said second level "b" of electrode current and measuring voltage at said reference cell at said second level "b" of electrode current, and
   deducing the polarization potential from said measured cell voltages and said measured levels "a" and "b" of electrode current .

2. The method of claim 1 wherein said measurements of cell voltage and electrode current at said second level of electrode current are made subsequent to a predetermined time ranging between about one millisecond and one second following said abrupt change to said second level of electrode current.

3. The method of claim 1 wherein rectifier means is used to produce said electrode current, said rectifier means incorporating an electrical filter therein for smoothing said electrode current and wherein said filter substantially affects said electrode current levels during modulation.

4. The method of claim 3 wherein said electrical filter introduces filtering of said electrode current with a time constant ranging between about 1 millisecond and 1 second.

5. The method of claim 1 wherein said modulation comprises at least one change of electrode current between said first level "a" of electrode current and said second level "b" of electrode current distinct from said first level "a" of electrode current, said first and second levels of electrode current being non-zero.

6. The method of claim 1 wherein the step of deducing the polarization potential of the structure comprises calculating an IR drop between said cell and said structure according to the formula $$V_{cIRA} = I_A \frac{V_{cb} - V_{ca}}{I_b - I_a}$$

where $V_{cIRA}$ represents said IR drop at steady state electrode current level $I_A$; $V_{cb}$ and $V_{ca}$ represent the measured voltages at said reference cell at levels "b" and "a" respectively of electrode current; and $I_b$ and $I_a$ represent said measured levels "b" and "a" respectively of electrode current.

7. The method of claim 6 wherein the values of $V_{cb}$, $V_{ca}$, $I_b$ and $I_a$ are composite values obtained from multiple current modulation cycles.

8. The method of claim 6 wherein one of the two measured levels $I_a$ and $I_b$ of electrode current equals the steady state current $I_A$.

9. The method of claim 1 wherein said deducing step comprises calculating said polarization potential from reference cell voltage at $I_A$ according to the formula $$V_p = V_{cA} - I_A \frac{V_{cb} - V_{ca}}{I_b - I_a}$$

where $V_P$ represents the polarization potential; $V_{cA}$ represents voltage at said reference cell at a steady state level of electrode current $I_A$; $V_{cb}$ and $V_{ca}$ represent the measured voltages at said reference cell at levels "b" and "a" respectively of electrode current; and $I_b$ and $I_a$ represent said measured levels "b" and "a" respectively of electrode current.

10. The method of claim 9 wherein the measurement system includes multiple reference cells positioned in the electrolyte and $V_{cA}$, $V_{ca}$, and $V_{cb}$ are composite values obtained from the multiple reference cells positioned within said electrolyte.

11. The method of claim 10 wherein said multiple reference cells are electrically connected.

12. The method of claim 1 wherein modulation of said electrode current is automatic and periodic.

13. The method of claim 1 wherein said electrode current modulation is performed by applying a current from a set of at least one electrode distinct from said electrode means used to protect said metal structure.

14. The method of claim 1 wherein said continuous flow of unidirectional current to said structure through said electrolyte is powered by adjustable rectifier means.

15. The method of claim 14 wherein said electrode current modulation varying step is performed by said adjustable rectifier means.

16. The method of claim 1 wherein said continuous flow of unidirectional current to said structure through said electrolyte is powered by adjustable direct current power source.

17. A method for automatically and continuously electrically protecting a metal structure positioned in a corroding electrolyte by maintaining the polarization potential of said structure substantially constant at a predetermined value, comprising:

continuously passing a flow of unidirectional current from adjustable direct current power source means to said structure through said electrolyte from electrode means positioned therein, establishing a measurement circuit comprising measurement means communicating between a single reference cell and said metal structure, said cell positioned in said electrolyte between said electrode means and a wall of said structure at a substantial distance therefrom, establishing a controller circuit comprising controller means communicating between said measurement circuit and said adjustable direct current power source means, measuring said electrode current at a first level "a" and measuring voltage at said reference cell at said first level "a" of electrode current, varying the electrode current by modulation which abruptly changes said electrode current from said first level "a" to a second level "b", measuring said second level "b" of electrode current and measuring voltage at said reference cell at said second level "b" of electrode current, and deducing the polarization potential from said measured cell voltages and said measured levels "a" and "b" of electrode current.

18. The method of claim 17 wherein said electrically protected metal structure is cathodically protected.

19. The method of claim 17 wherein said unidirectional current serves as a protective current.

20. The method of claim 17 wherein said controller means comprises microprocessor-based means.

21. A method for determining the polarization potential of a metal structure in contact with a corroding electrolyte to control a unidirectional flow of electrode current through the electrolyte between the structure and electrode means positioned within the electrolyte comprising the steps of:

establishing a measuring circuit comprising the structure, a single reference cell, voltage measuring means coupled with the cell and the structure for measuring voltage between the cell and the structure, and current measuring means for measuring the level of the electrode current, the single reference cell being positioned in the electrolyte between the electrode means and a wall of the structure and spaced from the structure and the electrode means, measuring a first level "a" of the electrode current and a first voltage of the single reference cell at the first level "a" of electrode current, varying the level of electrode current by modulation which abruptly changes the electrode current from the first level "a" to a second level "b", measuring the second level "b" of electrode current and measuring the voltage of the single reference cell at the second level "b" of electrode current, and combining at least the two measured reference cell voltages and the two measured levels of electrode current to determine polarization potential.

22. The method of claim 21 further comprising the step of continuously passing the unidirectional electrode current between the structure and the electrode means during the measuring steps.

23. The method of claim 21 further comprising the step of filtering the unidirectional electrode current to reduce electrical interference.

24. The method of claim 21 wherein said determining step comprises determining an IR drop between the reference cell and the structure according to the formula:

$$V_{cIRA} = I_A (V_{cb} - V_{ca})/(I_b - I_a)$$

where $V_{cIRA}$ represents the IR drop value between the reference cell and the structure at steady state electrode current level $I_A$; $V_{cb}$ and $V_{ca}$ represent the voltages at the reference cell at levels "b" and "a" respectively of electrode current, respectively; and $I_b$ and $I_a$ represent levels "b" and "a", respectively of electrode current.

25. The method of claim 24 wherein one of $I_a$ and $I_b$ equals $I_A$.

26. In a system for protecting a metallic structure in contact with a corroding electrolyte including electrode means immersed in the electrolyte and current means coupled with the electrode means and the structure for passing a unidirectional current between the structure and the electrode means, a control system for controlling the polarization potential of the metal structure comprising:

a single reference cell positioned in the electrolyte between the electrode means and a wall of the structure and spaced from the structure and the electrode means;

a measuring circuit including voltage measuring means coupled with the cell and the structure for measuring voltage between the single reference cell and the structure and current measuring means for measuring level of electrode current;

controller means communicating between said measurement circuit and said current means for varying electrode current by modulation which abruptly changes the electrode current level between a first level "a" and a second level "b";

the measuring circuit measuring the electrode current at both the first and second levels and the reference cell voltage at both the first and second levels of electrode current; and the controller means combining the measured first and second electrode current levels and measured cell voltages at the first and second electrode current levels to generate the polarization potential.

27. The system of claim 26 wherein the unidirectional current is passed continuously between the structure and the electrode means.

28. The system of claim 26 wherein said current means further comprises filtering means for filtering the unidirectional electrode current to reduce electrical interference.

29. The system of claim 26 wherein said controller means combines the measured first and second electrode current levels and measured cells voltages to determine an IR drop value between the reference cell and the structure according to the relation $$V_{cIRA} = I_A (V_{cb} - V_{ca})/(I_b - I_a)$$

where $V_{cIRA}$ represents the IR drop at steady state electrode current level $I_A$; $V_{cb}$ and $V_{ca}$ represent the voltages at the single reference cell at levels "b" and "a" respectively of electrode current; and $I_b$ and $I_a$ represent levels "b" and "a", respectively of electrode current.

30. The system of claim 29 wherein one of $I_a$ and $I_b$ equals $I_A$.

* * * * *

UNITED STATES PATENT AND TRADEMARK OFFICE
CERTIFICATE OF CORRECTION

PATENT NO. : 4,755,267

DATED : July 5, 1988

INVENTOR(S) : David N. Saunders

It is certified that error appears in the above-identified patent and that said Letters Patent is hereby corrected as shown below:

In the drawings, Sheet 1, Fig. 2, the reference numerals 40 and 46 should be reversed and the lead line from reference numeral 48 should be extended to the presently unnumbered wire extending between newly numbered terminal 46 and the structure 10.

Signed and Sealed this

Seventh Day of February, 1989

*Attest:*

DONALD J. QUIGG

*Attesting Officer*  *Commissioner of Patents and Trademarks*